United States Patent
Baba et al.

(10) Patent No.: US 6,665,561 B2
(45) Date of Patent: Dec. 16, 2003

(54) FEMALE PHYSICAL CONDITION MANAGING APPARATUS

(75) Inventors: Michiko Baba, Shiraoka-Machi (JP); Tamaki Shoji, Asaka (JP); Miyuki Kodama, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/968,036

(22) Filed: Oct. 2, 2001

(65) Prior Publication Data

US 2002/0013521 A1 Jan. 31, 2002

(30) Foreign Application Priority Data

Feb. 10, 2000 (JP) ........................................ 2000-302756
Feb. 10, 2000 (JP) ........................................ 2000-312434

(51) Int. Cl.[7] ................................................ A61B 5/05
(52) U.S. Cl. ........................................ 600/547; 600/551
(58) Field of Search ................................ 600/547, 551, 600/587, 591, 300, 304

(56) References Cited

U.S. PATENT DOCUMENTS 4,685,471 A * 8/1987 Regas et al. ................. 600/547
5,916,173 A * 6/1999 Kirsner ....................... 600/551
6,402,699 B1 * 6/2002 Kodama et al. ............. 600/551

FOREIGN PATENT DOCUMENTS

| EP | 0 498 303 | 8/1992 |
| EP | 1084676 A1 | 3/2001 |
| JP | 10-364563 | 12/1998 |
| JP | 11-258538 | 9/1999 |

* cited by examiner

*Primary Examiner*—Eric F. Winakur
*Assistant Examiner*—Jonathan Foreman
(74) *Attorney, Agent, or Firm*—McDermott, Will & Emery

(57) ABSTRACT

Disclosed is a female physical condition managing apparatus, which permits a female user to make a quick decision as to which physical phase of the monthly body condition she has presently in terms of how the value of BI is changing. Also, an advisory message appropriate for health care is given to her. For example, the degree of swelling appearing for the PMS period is determined, and a most appropriate advice is given to her. Likewise, she can be advised while continuously watching the difference between the present weight and the target weight. The values of BI measured every day are shown in the form of graph, accompanying pieces of information of physical condition as determined.

13 Claims, 14 Drawing Sheets

FIG.5

| PERIOD | ADVISORY CONTENT |
|---|---|
| First Divisional Period (Menstruation Period) | 11. Ingest iron-rich foods. Liver and spinach are most recommendable.<br>12. A chill will increase pain. Thus, don't let your body become cole.<br>13. Your skin is very sensitive at present. Thus, wash your face and hair gently. |
| Second Divisional Period ("In good condition"Period) | 21. Your skin is in good condition. However, careful treatment is still required.<br>22. You are vigorous enough to continue hard work more or less. Thus please enjoy yourself.<br>23. Think more positively about yourself by taking positive actions everywhere. |
| Third Divisional Period (Delicate Period) | 31. Melanosisis is noticeable. Vitamin C is effective to suppress it.<br>32. Work hard if you think you are eating too much.<br>33. Take care of pimples if you start to be anxious about them. |
| Fourth Divisional Period ("In poor condition"Period) | 41. Weight increases easily. Refrain from taking salted foods.<br>42. Get a lot of sleep.<br>43. Clean your skin and keep it moist. |
| Fifth Divisional Period(Pregnancy -possible Period) | 51. You may have a slight pain in your underbelly for a while.<br>52. You may have a photoflash or a hot flash.<br>53. If you want to have a baby, this time would be your best chance to do so. |
| Time of "PMS" | 61. A small amount of swelling appears. Refrain from taking salted foods.<br>62. Take care of the swelling. Eating pumpkin and sweet potatoes are recommendable for this purpose.<br>63. Significant amount of swelling appears. Drinking water rich in minerals is recommendable for this purpose. |

FIG. 7

| Weight Level | First Divisional Period | Second Divisional Period | Third Divisional Period | Fourth Divisional Period |
|---|---|---|---|---|
| Weight Level 1 | 11. Your weight starts decreasing naturally quite soon. Don't worry about your weight increasing. 12. Your weight increases, but not so much that you have to worry about it. Please relax. | 13. Your body condition is good. Do light exercising. Keep a positive attitude at all times. 14. You can attain the weight you desired soon. Eat good food and take a good exercise. | 15. You have almost attained your desired weight. How about eating normally and taking a walk? 16. The amount of energy you are consuming is increasing. Continue exercising until you have achieved your desired weight. | 17. The amount of water in your body is apt to increase, and therefore, you may feel that your weight has increased a little. However, your weight does not increase so much that you have to be anxious about it. 18. The amount of energy you are consuming is decreasing. Maintain your present weight. |
| Weight Level 2 | 21. It is best for you to relax. Start exercising after termination of your menstruation period. 22. Wait for the swelling to disappear. Lead a regular life. | 23. Your body condition is so good that you can take positive actions everywhere. You can continue dieting. 24. Your mental and physical condition is good. You can take positive actions about dieting and everything else. | 25. This time would be the best time to start dieting. Reduce your weight by doing light jogging. 26. The amount of energy you are consuming is increasing. Do exercising to decrease your weight until you attain your desired weight. | 27. Your body condition is gradually getting worse, and it is difficult to reduce your weight. Take it easy. 28. An adverse effect may be caused if you do too much dieting. Suspending your dieting may have a good effect on your body. |
| Weight Level 3 | 31. It will take a long time to attain your desired weight. Take it easy, and proceed with your dieting slow but steady. 32. Start exercising when your body condition becomes good enough. Continue exercising until you have attained your desired weight. | 33. You have to lose a lot of weight before attaining your desired weight. Consume an increased amount of calorie by doing a lot of exercise. 34. Your way of trying to reduce your weight is not very effective, and thus, it may take you a long time to attain your desired weight. Take well-balanced meals and do as much exercise as you can. | 35. This time would be the best time to start dieting. Do as much exercising as you can. The amount of energy you are consuming is increasing. This time would be the best time to start dieting. | 37. If your body condition is good, do some exercising, although no satisfactory effect may result. 38. You may have a good appetite. Be careful of eating too much lest your weight increase. |

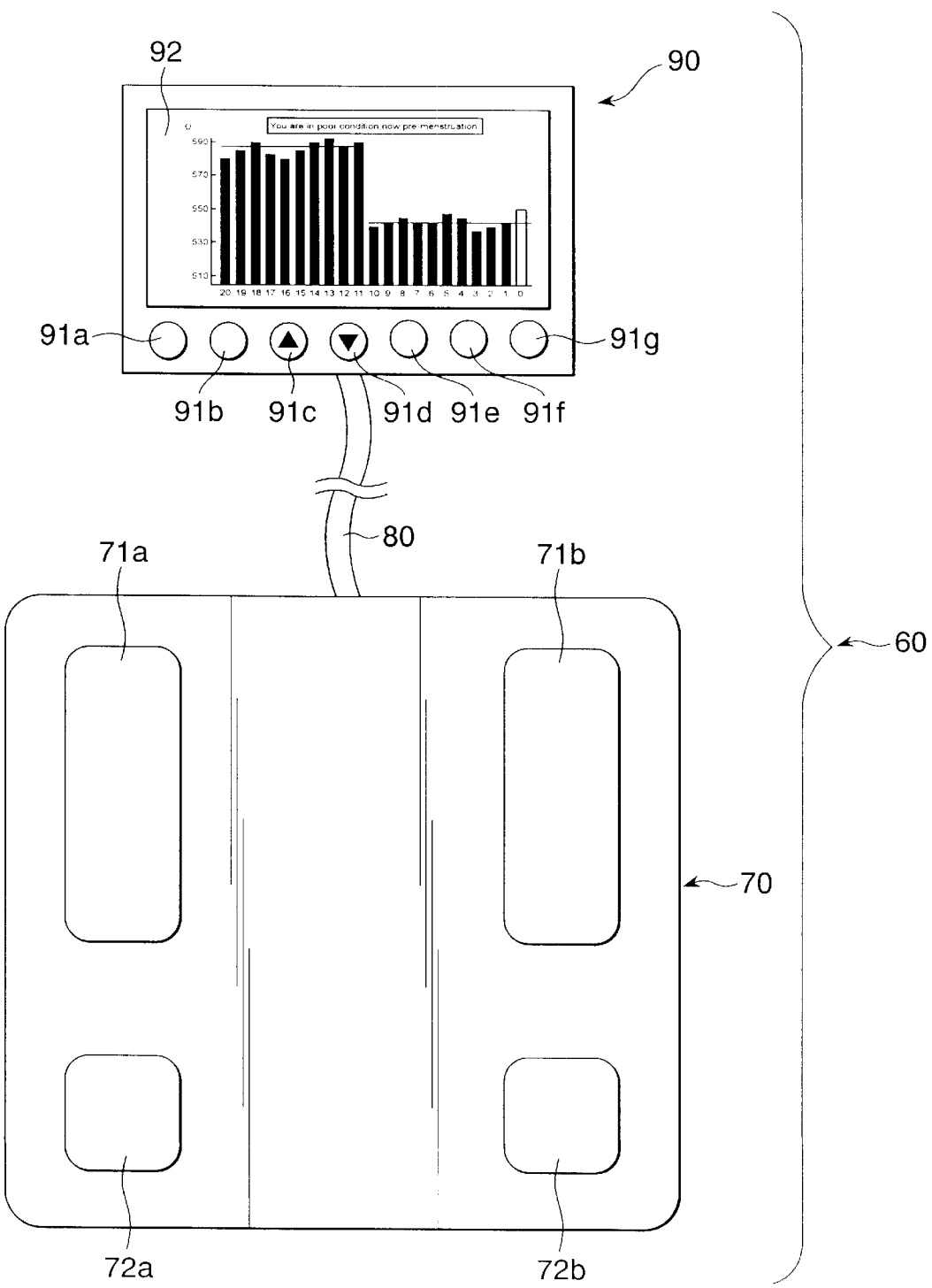

FEMALE PHYSICAL CONDITION MANAGING APPARATUS

BACKGROUND OF THE INVENTION

1. Field of the Invention

The present invention relates to a female physical condition managing apparatus which permits women to make a decision about the monthly physical condition in which there appear a set of physical effects that women feels less pleasing on the ovulation day, at the time they have the premenstrual syndrome (hereinafter abbreviated as "PMS") or for the pregnancy-possible period.

2. Prior Art

The women's monthly physical condition is related closely with their body temperature. The body temperature transfers from the low-temperature period to the high-temperature period on the ovulation day, and from the high-temperature to the low-temperature period on the beginning day of the menstruation period.

In the monthly physical condition different aspects appear in four divisional periods, that is, the menstruation period, the post-menstruation period, the post-ovulation period and the pre-menstruation period. In these different aspects women are said to have a variety of mental and physical effects, as for instance, follows: women are liable to have an increased quantity of water or fat in their bodies with the result that their weights increase 1 to 3 kilograms.

Women have the PMS seven days prior to the beginning of the menstruation period, causing most women to suffer from headache, irritation, stomach trouble, swell or any other unpleasing symptom. It is said that if they are on a diet while being in poor condition, the stress increases, and that as a counter action they eat a lot of food.

Also, it is said that they relax by realizing that such unpleasing aspect is attributable to the PMS, accepting it as a token of proving that they are in good health.

Recently the dieting has been popular as effective means for women to become thinner. Women on a diet must continue limiting the amount and type of food that they eat in order to become thinner, paying little or no consideration to their mental or physical conditions. The practice of limiting the amount and type of food while they are in poor condition or unstable in mind will burden their bodies badly. Particularly some adverse effects will be caused on their physical conditions as for instance, follows: their skin loses an attractive shiny appearance; their hair loses luster; their nails are easily broken.

Even though women are not on a diet, they are liable to have such unpleasing effects cyclically owing to monthly endocrine disorders in their bodies. In the hope of improving their physical conditions they are inclined to take excessive amounts of certain medicines or particular types of food to cause side effects on their bodies. Otherwise, excessive making-up causes their skin to get worse.

A set of symptoms including appearance of the swelling will be caused at the time they have the PMS, but there has been no means to realize that they are having the PMS rather than particular disease. The incapability of realizing the situation has been annoying women.

In view of the above what is aimed at by the present invention is to permit women to: make a correct decision about their physical condition; and have a good advice how to deal with the so determined physical condition, thereby allowing them to release from their anxieties and reducing the burden on their mind. This is really the case with the anxieties at the time they have the PMS. Also, such remedy is most effective to allow women to continue dieting efficiently.

As described above the women's monthly physical condition is related closely with their body temperature. The body temperature transfers from the low-temperature period to the high-temperature period on the ovulation day, and from the high-temperature to the low-temperature period on the beginning day of the menstruation period. Also, as described above, in the monthly physical condition different aspects appear in four divisional periods, that is, the menstruation period, the post-menstruation period, the post-ovulation period and the pre-menstruation period, and in these different aspects women are said to have a variety of mental and physical effects.

As is well known, women can presume when they will have ovulation days and menstruation periods by measuring their body temperatures each and every day with body thermometers.

The body temperatures thus measured can be recorded in the form of graphs, which dearly show the transition from the high-temperature period to the low-temperature period or inversely from the low-temperature period to the high-temperature period. From such graphic presentation women learn that two different aspects appear in the monthly physical condition. Appearance of two different aspects proves that their bodies are in normal condition, making women learn that the rhythmic variation of physical condition is normal.

Also, such body temperature can be recorded in the form of tables. This type of recording is adopted by doctors and other medical experts for the purpose of making a decision about their patients' physical conditions.

Such graphic presentation of body temperature is useful in healthcare, but recording body temperature each and every day is not easy to continue. Women take their body temperature every morning in bed by putting and holding their thermometers in their mouths a few minutes, and they must make manually a graphic record or table showing how the body temperature varies every day. Women often fall in sleep while taking their body temperature in bed.

Women are busy after getting up in the morning, having no sufficient time left for measuring and recording their body temperature. As a result there appear blanks here and there in the graph, and such In view of the above what is aimed at by the present invention is to permit women to readily determine which stage of the monthly physical condition has been reached by making a simple measurement, the result of which is displayed quickly in easily understandable fashion. Thus, they can be released from unnecessary anxieties, realizing that they are in normal condition.

SUMMARY OF THE INVENTION

Japan Patent Application No. H-11-258358, which patent application was filed by the same applicant as the present patent application, proposed an apparatus for measuring the value of bioelectrical impedance hereinafter, the term, "bioelectrical impedance" abbreviated as "BI") and for making a decision about the monthly body condition on the basis of BI thus measured. The value of BI is closely related with the body temperature, remaining high for the period for which the body temperature remains low whereas remaining low for the period for which the body temperature remains high. After rising before the beginning of the menstruation period the body temperature descends, and it remains low in the early half of the menstruation period.

To achieve the first aim or objective as described above a female physical condition managing apparatus according to a first aspect of the present invention is so designed that it uses the relation between the BI and the monthly physical condition to make a decision about the monthly physical condition in terms of the measured BI values, selecting a most appropriate advisory message from those prepared beforehand and giving the so selected advisory message to a woman who is using the apparatus. Specifically at the time the woman has the PMS, the degree of swelling is determined in terms of the measured value of BI, and then a most appropriate advice is given to the woman. Also, the woman can be given a most appropriate advice, which is prepared by taking into consideration the present physical condition and the difference between the present weight and the weight she desires.

Specifically a female physical condition managing apparatus according to the first aspect of the present invention comprises: a bioelectrical impedance meter for measuring the value of BI of a woman who is using the apparatus; an advice storing device for storing a plurality of advisory messages for each of the specific divisional periods characteristic of the different phases which are noticeable from the monthly body condition of the woman; a decision-making unit for making a decision as to which specific divisional period the woman is passing over on the basis of the time-series transition of BI; an advising unit responsive to the decision-making of which specific divisional period for retrieving appropriate advisory messages from the advise storing device; and an informing unit for informing the woman of the so retrieved advisory messages.

The advice storing device may have advisory messages stored for each of the first divisional period spanning from the beginning day to the ending day of the menstruation period, the second divisional period spanning from the day subsequent to the termination of the menstruation period to the ovulation day, the third divisional period spanning from the ovulation day to the specific day one week earlier than the beginning of next menstruation period presumable from the record, and the fourth divisional period spanning from the specific day to the beginning day of next menstruation period.

The advice storing device may have advisory messages stored for the fifth pregnancy-possible period.

The decision-making unit may include a swelling determining unit, which is responsive to the decision-making of the present period being the fourth divisional period for determining the degree of swelling in terms of the value of BI determined by the bioelectrical impedance meter, and for retrieving the most appropriate advisory message from the advise storing device.

The female physical condition managing apparatus may further comprise: an inputting unit for setting and inputting a desired weight; a weight scale for measuring the present weight; and a weight-difference arithmetic unit for determining the difference between the desired weight and the present weight, whereby the advising unit may retrieve appropriate advisory messages from the advise storing device on the basis of the difference between the desired weight and the present weight and the divisional period representing the current body condition.

The value of BI may be the one modified with the weight measured by the weight scale.

The appropriate advisory messages may pertain to the weight and the dieting.

In a case where the divisional period determined by the decision-making unit is the third divisional period, the appropriate advisory messages pertaining to the weight and the dieting may induce the woman to perform the dieting positively.

To achieve the second aim or objective as described above a female physical condition managing apparatus according to the second aspect of the present invention is so designed that it uses the relation between the BI and the monthly physical condition (see Japan Patent Application No. H-11-258358) to permit a woman using the apparatus to make a decision as to whether her body is in good condition in terms of the values of BI, which are measured each and every day to provide graphic presentations showing how such factor varies with time.

Specifically a female physical condition managing apparatus according to the second aspect of the present invention comprises: a bioelectrical impedance meter for measuring the value of BI of a woman who is using the apparatus; a bioelectrical impedance memory for storing the measured values of BI; an arithmetic unit for calculating the mean value of the values of BI stored for the period for which the BI remains at raised values and the mean value of those stored for the period for which the BI remains at lowered values; and a display for displaying the time-sequence transition of the stored BI values in the form of graphs, and for displaying the mean values of the raised values of BI and the lowered values of BI in the form of graphs.

A female physical condition managing apparatus according to the third aspect of the present invention comprises: a bioelectrical impedance meter for measuring the value of BI of a woman who is using the apparatus; a bioelectrical impedance memory for storing the measured values of BI; and a display for displaying the time-sequence transition of the recorded values of BI in the form of graphs, representing time in abscissas and the values of BI in ordinates, the value of BI increasing with the descending distance toward the axis of abscissas, whereby the envelope of the raised values of BI may be low whereas the envelope of the lowered values of BI may be high.

The female physical condition managing apparatus may further comprise a decision-making unit for making a decision on which specific divisional period of the monthly physical condition the woman is passing over on the basis of the time-sequence transition of BI, allowing the display to show the present physical condition along with the graphic presentation.

The female physical condition managing apparatus may further comprise a decision-making unit for making a decision on which specific divisional period of the monthly physical condition the woman is passing over on the basis of the time-sequence transition of BI; and a physical condition memory for storing the physical conditions determined by the decision-making unit, thus allowing the display to show in the graphic presentation, the divisional period for which the woman has passed over for reference.

The female physical condition managing apparatus may further comprise a body temperature presuming unit for making a decision as to whether the body temperature varies in the high-temperature period or the low-temperature period from the time-sequence transition of the BI values stored in the bioelectrical impedance memory, whereby the display is made to indicate in the graphic presentation, the high-temperature period or the low-temperature period thus presumed by the body temperature presuming unit.

A female physical condition managing apparatus according to the fourth aspect of the present invention comprises:

a bioelectrical impedance meter for measuring the value of BI of a woman who is using the apparatus; a bioelectrical impedance memory for storing the measured values of BI;

an arithmetic unit for calculating the mean values per monthly period of the BI values of the high-temperature period and of those of the low-temperature period with reference the monthly physical condition of the woman; and a display for showing the mean values of the BI values of the high-temperature period and those of the low-temperature period in each of plural monthly periods in the form of graph.

Other objects and advantages of the present invention will be understood from the following description of preferred embodiments of the present invention, which are shown in accompanying drawings:

FIG. 5 is a collection of advisory messages in the female physical condition managing apparatus of FIG. 1;

FIG. 7 is a collection of advisory messages in the female physical condition managing apparatus according to the second embodiment;

FIG. 8 illustrates a female physical condition managing apparatus according to a third embodiment of the present invention in appearance;

DESCRIPTION OF PREFERRED EMBODIMENTS

Figure 1:
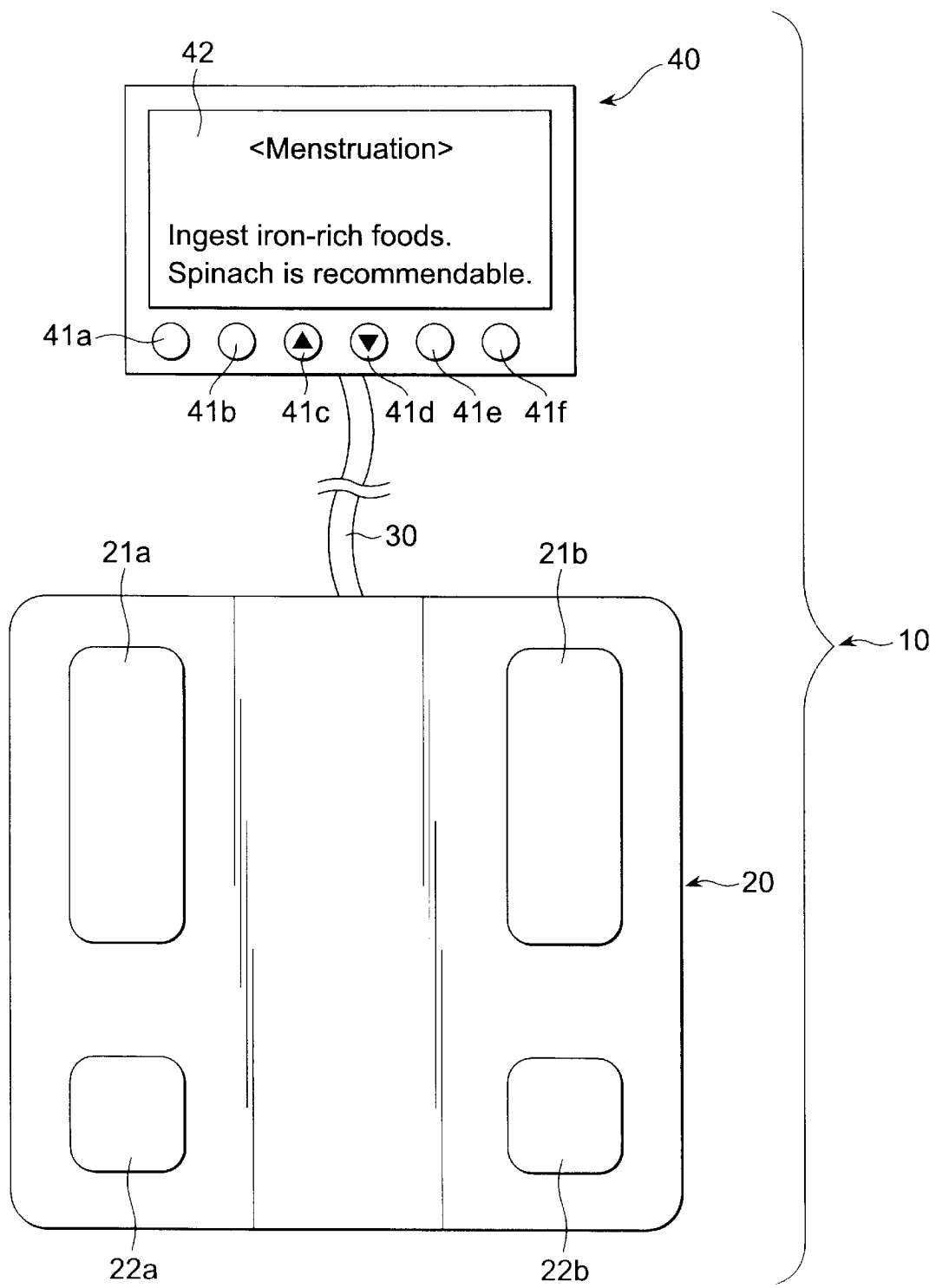
FIG. 1 illustrates a female physical condition managing apparatus according to a first embodiment of the present invention in appearance.

Referring to FIG. 1, a female physical condition managing apparatus 10 according to the first embodiment comprises a scale-and-bioelectrical impedance meter 20 and a control box 40 connected to the scale-and-bioelectrical impedance via an electric cable 30 or via infrared or electromagnetic wave.

The scale-and-bioelectrical impedance meter 20 has constant current feeding electrodes 21a and 21b and voltage measuring electrodes 22a and 22b provided on its front side whereas the control box 40 has a set of operation buttons 41a to 41f and a display 42 provided on its front side. The set of operation buttons include a power source button 41a, a measurement button 41b, an UP digit-shifting button 41c, a DOWN digit-shifting button 41d, a "menstruation beginning day" inputting button 41e and a setting button 41f.

Figure 2:
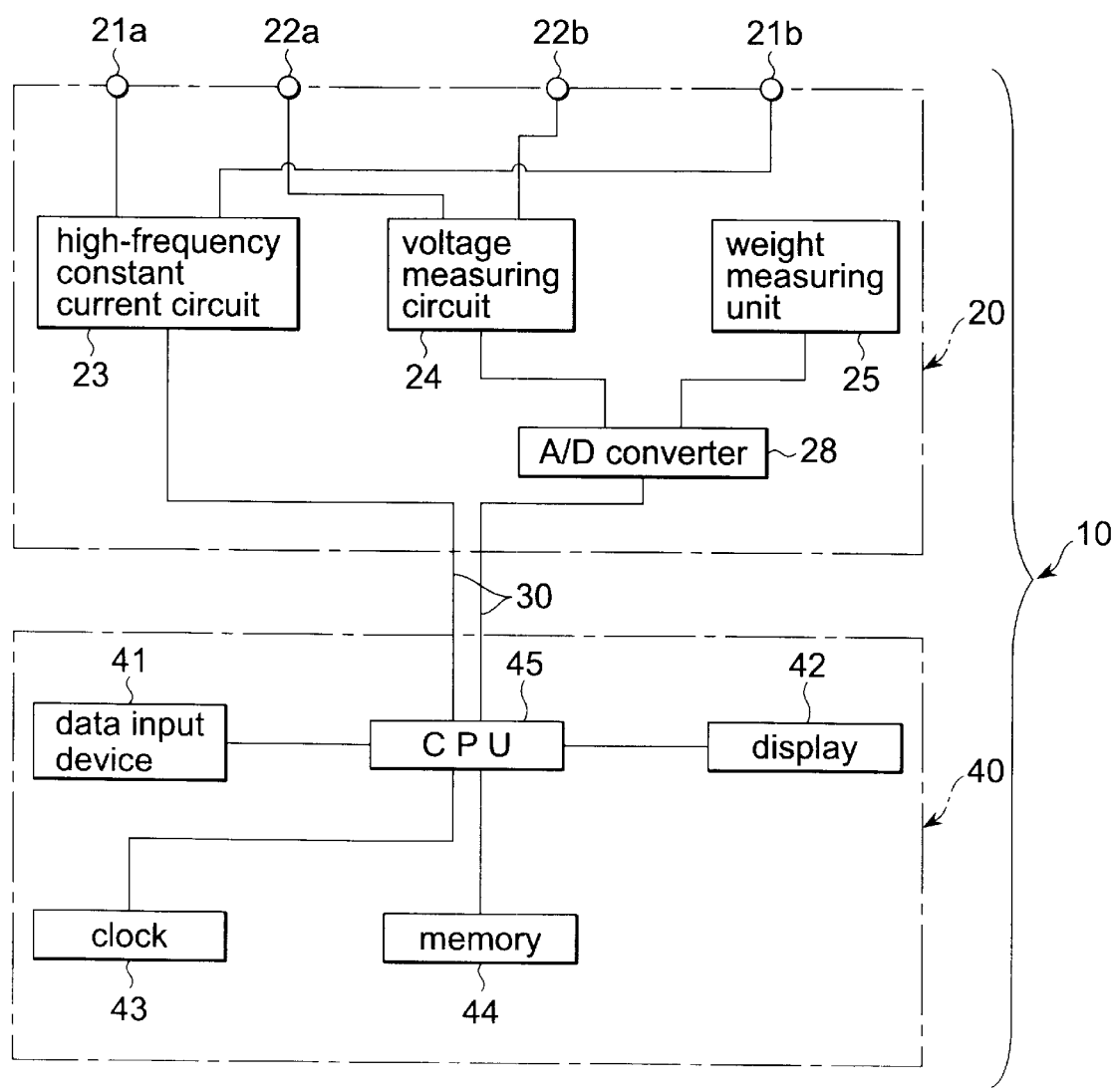
FIG. 2 is a block diagram showing how different functions make up the female physical condition managing apparatus of FIG. 1.

FIG. 2 shows the functional structure of the female physical condition managing apparatus 10. As shown in the drawing, the scale-and bioelectrical impedance meter 20 comprises a high-frequency constant current circuit 23 for supplying a weak high-frequency current of fixed value to the constant current feeding electrodes 21a and 21b, a voltage measuring circuit 24 for measuring the voltage appearing between the voltage measuring electrodes 22a and 22b, a weight measuring unit 25, and an A/D converter 28 for converting the measured voltage and weight to digital values.

The control box 40 comprises a data input device 41 including a set of operation buttons 41a to 41f for inputting instructions for measurement, data pertaining to the menstruation period and other pieces of information, a display 42 for showing the time-sequence transition of measured BI values, the body condition and such like, a clock 43 for determining the date and time on or at which the measurement is effected, a memory 44 for storing the measured BI values, the measurement date and time and a plurality of advisory messages, and a CPU 45, which takes not only the arithmetic and advisory message-selecting parts of: making a decision on the female physical condition on the basis of data pertaining to the menstruation period inputted by the data input device 41, the measured BI values and the weight; and selecting and storing data in the memory or selecting and showing data in the display 42, but also the part of determining the degree of swelling.

In this particular embodiment the scale-and-bioelectrical impedance meter 20 and the control box 40 are separate, together making up the female physical condition managing apparatus. The CPU 45 may be installed in the scale-and-bioelectrical impedance meter 20. Otherwise, the scale-and-bioelectrical impedance meter 20 and the control box 40 may be combined as a whole.

Now, the manner in which the female physical condition managing apparatus works is described.

Figure 3:
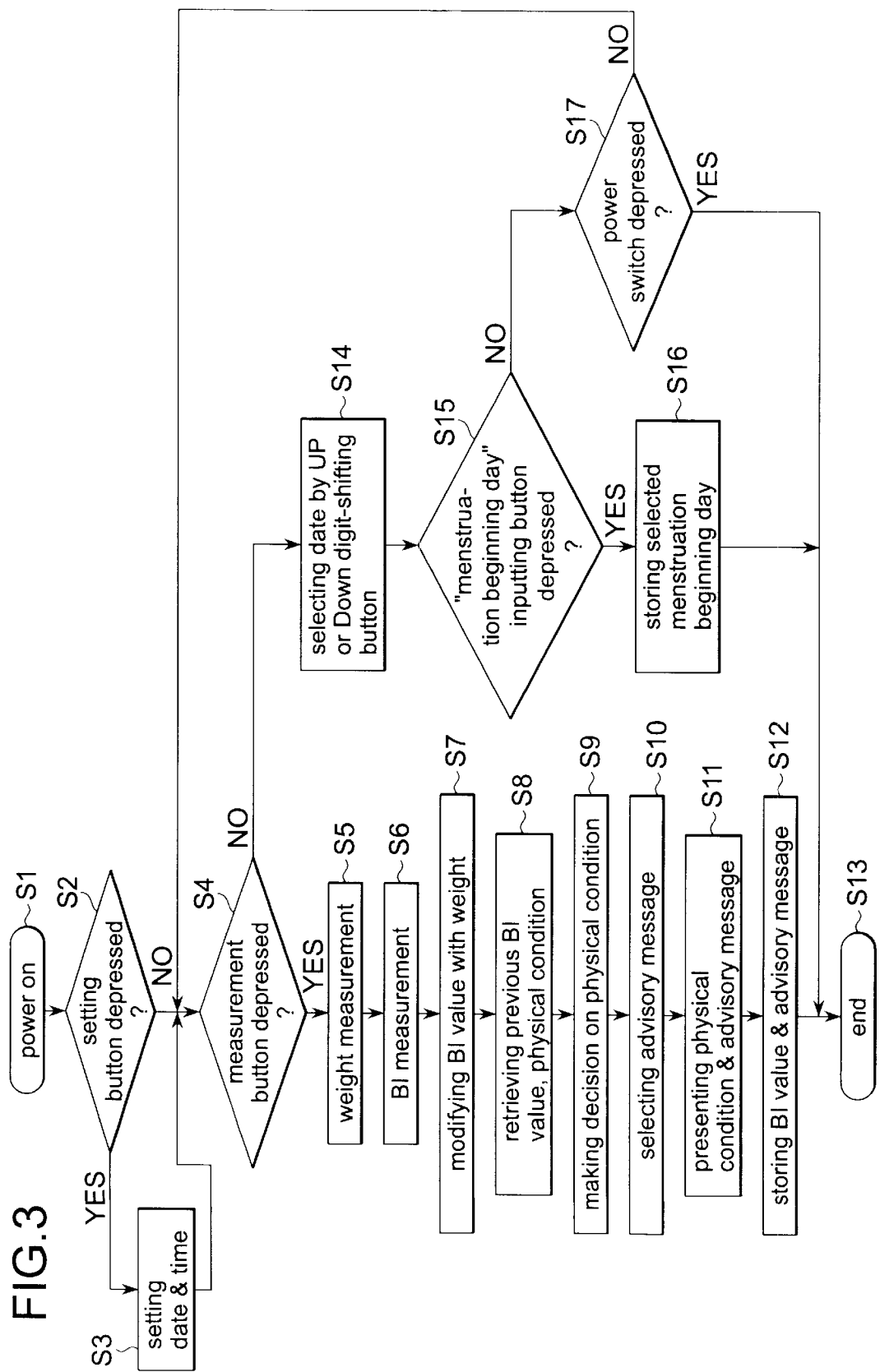
FIG. 3 is a flowchart showing the proceeding according to which the female physical condition managing apparatus of FIG. 1 works.

FIG. 3 is a flow chart showing the sequential steps to follow in making a decision on the monthly physical condition of a woman who is using the apparatus 10. The woman depresses the power source switch 41a at STEP 1, thus putting the apparatus 10 in circuit with the power supply. Depression of the setting button 41f at STEP 2 puts the apparatus 10 in the setting mode, proceeding to Step 3 where the present date and time is set. Specifically the digits representing date and time are changed by using the UP digit-shifting button 41c and the DOWN digit-shifting button 41d until the present date and time appears in the display. Then, the present date and time is set by depressing the setting button 41f again. Likewise, the beginning day of the previous menstruation period is inputted and set.

Depression of the measurement button 41b at STEP 4 puts the apparatus 10 in the measurement mode, proceeding to STEP S5. If not, the apparatus is put in the menstruation data inputting mode, proceeding to STEP 14

The measurement mode starts from STEP 5. The woman stands on her barefeet on the bioelectrical impedance meter 20 equipped with the weight scale. Specifically she stands on the weight scale with the toes and heels of the left and right feet put on the constant current feeding electrodes 21a and 21b and the voltage measuring electrodes 22a and 22b respectively. Then, the measurement starts with the weight of the woman.

At STEP 6 the high-frequency constant current circuit 23 makes a high-frequency, weak current flow in her body via the constant current feeding electrode 21a, the toe of the left foot, the left leg, the lower part of her abdomen, the right leg, the toe of the right foot and the constant current feeding electrode 21b. The voltage measuring circuit 24 determines the voltage appealing between the voltage measuring electrodes 22a and 22b, thus determining the BI value. At STEP 7 the BI value is modified with weight according to the following equation 1 or 2:

$$BI \text{ modified with weight} = BI + A \times (\text{difference of weight from the initial weight}), \quad (1)$$

or $$BI \text{ modified with weight} = BI + B \times (\text{difference of weight from the preceding weight}) \quad (2)$$

where "A" and "B" stand for correction coefficients.

The so modified BI value is independent from the influence caused by the varying weight.

At STEP 8 the BI values measured on several days before the present day, the physical condition determined on the day before the present day, some data pertaining to the beginning day of the last menstruation period and other data are retrieved from the memory 44 to be put in the CPU 45.

At STEP 9 the CPU 45 makes, on the basis of the relation between the BI values and the monthly body condition as described earlier, a decision as to which divisional period the woman is passing over, the first divisional period (the menstruation period), the second divisional period (the "in good condition" period), the third divisional period (the "not changing" period), the fourth divisional period (the "in poor condition" period) or the fifth divisional period (the pregnancy-possible period).

The following example of divisional periods may fit women whose menstruation period lasts 28 days. It, however, should be noted that it depends on individuals how long each divisional period lasts.

Figure 4:
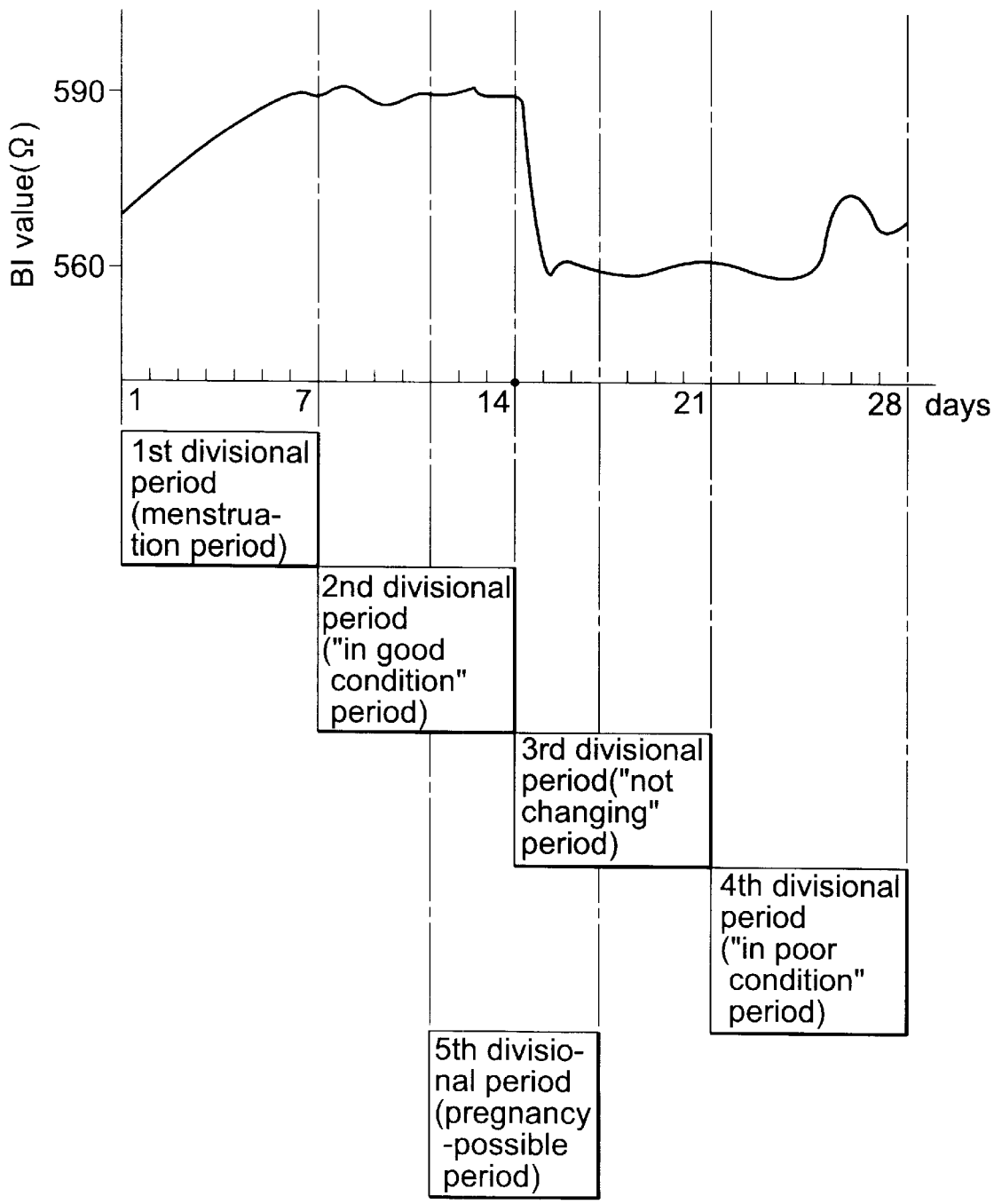
FIG. 4 illustrates what different physical phases appear monthly in women's bodies.

Referring to FIG. 4, the manner in which a decision is made on which divisional period the woman is passing over is described.

The seven days counted forward from the beginning day of the menstruation period are included in the "First Divisional Period" (the menstruation period). The "Second Divisional Period" (the "in Good Condition" Period) spans from the day following the termination of the "First Divisional Period" to the transient day on which the BI transfers from the raised value to the lowered value. The seven days counted forward from the transient day make up the "Third Divisional Period" (the "not changing" period). The day subsequent to the termination of the "Third Divisional Period" to the beginning day of next menstruation period are included in the "Fourth Divisional Period" (the "in poor condition" period). Finally, the "Fifth Divisional Period" (the pregnancy-possible period) includes three days before and after the transient day on which the BI transfers from the raised value to the lowered value. The transfer to the lowered value of BI is determined by detecting the decrease of 4 or more percent with respect to the mean value of the raised values of BI lasting some days just before the transient day.

Appearance of swelling is determined when detecting one or more percent decrease in the BI value with respect to the mean value of the previous BI values determined during the "Fourth Divisional Period" (the "in poor condition" period). The degree of swelling is assumed to be Level 1 for one percent decrease, Level 2 for two percent decrease, Level 3 for three percent decrease, and so forth.

As for the woman whose BI values were plotted in FIG. 4 the mean value of raised BI values is about 590 ohms, and the mean value of lowered BI values is about 560 ohms. Accordingly the BI curve is assumed to descend when detecting the BI value of 566.4 or less ohms, which is 4% lower than 590 ohms. The lowered value of BI was detected on the 15th day, and the pregnancy-possible period includes three days before and after the day.

The mean value of BI values measured during the Fourth Divisional Period is about 560 ohms. When detecting that the BI value is 554.4 ohms (one percent decrease) the degree of swelling is Level 1; when detecting that the BI value is 544.8 ohms (two percent decrease) the degree of swelling is Level 2; when detecting that the BI value is 543.2 ohms (three percent decrease) the degree of swelling is Level 3; and so forth.

In summary the month within which women have different physical effects is divided as follows:

the beginning day of the last menstruation period retrieved from the record and inputted is assumed to be the beginning day of the coming menstruation period;

the First Divisional Period (the menstruation period) starting from the beginning day of the menstruation period and lasting seven days;

the Second Divisional Period (the "in good condition" period) starting from the day subsequent to termination of the First Divisional Period to the day before the day on which four percent decrease is detected with respect to the mean value of the BI values measured in the second period;

the Third Divisional Period (the "not changing" period) starting from the day subsequent to termination of the Second Divisional Period to the day one week earlier than the beginning day of next menstruation period presumed from the record; and the Fourth Divisional Period (the "in poor condition" period) starting from the day subsequent to termination of the Third Divisional Period and ending with the day on which the beginning day of the menstruation period is retrieved from the record and inputted next time.

The days are counted backward from the beginning day each of some selected menstruation periods to a selected ovulation day both retrieved from the record, and on the basis of the average number of the so counted days the ovulation day is presumed and determined. Then, the Fifth Divisional Period (the pregnancy possible period) is determined as containing three days before and after the so presumed ovulation day. In FIG. 4, the ovulation day happens to fall on the 14th day earlier than the presumed beginning day of next menstruation period. The ovulation day must be corrected at the time the transition from the raised BI value to the lowered BI value is actually detected. Specifically if the transition is detected to be earlier than the presumed ovulation day, the Fifth Divisional Period (the pregnancy-possible period) is determined as including the three days subsequent to the transition day thus confirmed. Conversely no transition is detected actually after the presumed ovulation day, and then the pregnancy-possible period is deemed to last three days from the actual ovulation day.

Thus, the woman using the apparatus 10 can realize which stage has been reached, so that she may expect what bodily condition appears tomorrow and subsequent days. A decision making is not permitted if the values of BI measured during the last period are not available from the memory. In a case where no data is available the display 42 shows the message to this effect.

At STEP 10 the CPU 45 responds to the decision-making at STEP 9 for selecting an advisory message most appropriate for the decision-making among those stored in the memory 44, thus allowing the display 42 to show the so selected advisory message. The CPU 45 identifies the advisory message in terms of their identification numbers to prevent same advisory message as shown lately from being repeated.

At STEP 11 the display 42 shows the body condition and the advisory message. Specifically the display 42 shows the woman's body condition appealing in each divisional period, as for instance, follows: the menstruation period in the First Divisional Period, the "in good condition" period in the Second Divisional Period, termination of the ovulation or the "not changing" period in the Third Divisional period, the PMS period or "in poor condition" period in the Fourth Period, and the pregnancy-possible period in the Fifth Divisional Period.

Examples of advisory messages are: "Be careful as you may have unpleasing effects characteristic of pre-menstruation including swelling or irritation. Having vitamin B is recommendable for the purpose of reducing such effects." "Now you have some unpleasing effect in your body while the menstruation period is still lasting. It will end soon. Be careful of anemia. Having iron-rich foods is recommendable as a remedy." "The menstruation period has been terminated. You are in good condition. Do exercising positively."; or "You are being in the course of ovulation. Your body condition is descending. Be careful of not eating much.". In a case where two adjacent divisional periods overlap (12th to 16th days in FIG. 4), appropriate advisory messages pertaining to the adjacent divisional periods are selected among those in the memory to show them simultaneously or one after another. FIG. 5 shows three advisory messages for each divisional period. The memory 44 contains a lot of advisory messages.

At STEP 12 the weight-modified BI value measured this time, the present body condition, the date of measurement, the identification numbers of the advisory messages actually shown and some other data are stored in the memory 44. Then, at STEP 13 the power supply turns off automatically, and the measurement ends.

At STEP 14 the menstruation data inputting mode starts. A desired date is given in the display 42 by depressing the UP digit-shifting button 41c and the DOWN digit-shifting button 41d. At STEP 15 a decision is made as to whether or not the menstruation beginning day inputting button 41e was depressed. In the affirmative, the date selected at STEP 14 is stored in the memory 44 as the beginning day of the menstruation period. In the negative, at STEP 17 a decision is made as to whether or not the power source button 41a was depressed. In the affirmative, the power supply turns off at STEP 13, and the inputting of data is finished.

Now, a female physical condition managing apparatus 10 according to the second embodiment is described. A weight which is desired by a woman who is using the apparatus 10 can be set, and an advisory message can be selected and given in terms of the difference between the desired weight and the present weight. It is said that women's basal metabolic rate rises after the ovulation day. Women's body temperature rises after the ovulation day, and accordingly the basal metabolic rate rises, too. This is the time the exercise efficiency and hence, the amount of calorie women are consuming by exercising increases, and therefore it is best for women to do dieting. For the length of time spanning from the day one week earlier than the beginning day of the menstruation period to the last day of the early part of the menstruation period the basal metabolic rate descends, and the exercise efficiency lowers. Exercising causes no satisfactory effect. The amount of water in women's bodies is apt to increase, and the swelling is apt to appear. However, they need not to worry about their weight even though it increases more or less. It is said that it is best to relax. For the length of time starting from termination of the menstruation period, including the ovulation period women are in good condition, and it is better that they keep a positive attitude at all times, and that this time be recommendable for dieting.

In view of the above, an advisory message which positively recommends dieting to the woman is presented for the Third Divisional Period subsequent to the ovulation day (the "not changing" period); an advisory message which requests the woman to refrain exercising is presented for the Fourth Divisional Period including the week prior to the beginning day of the menstruation period (the "in poor condition" period); and an advisory message which positively recommends dieting and other activities to the woman is presented for the Second Divisional Period lasting from termination of the menstruation period to the ovulation day ( the "in good condition").

The female physical condition managing apparatus 10 according to the second embodiment and the functional construction of the apparatus 10 are same as shown in FIGS. 1 and 2 and described above with reference to these drawings.

The manner in which the female physical condition managing apparatus 10 according to the second embodiment works is described below.

Figure 6:
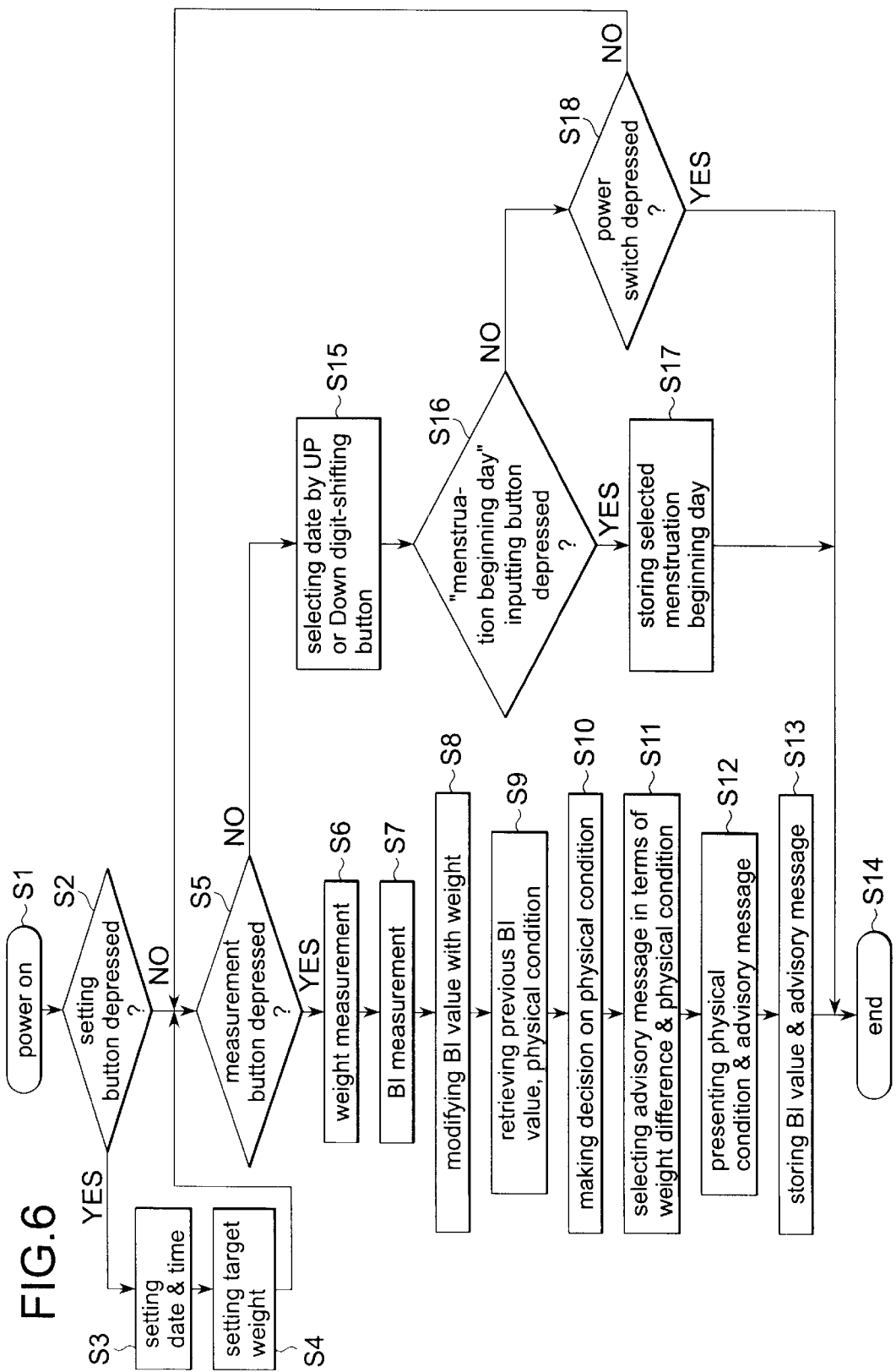
FIG. 6 is another flowchart showing the proceeding according to which a female physical condition managing apparatus according to a second embodiment works.

FIG. 6 is a flow chart showing the sequential steps to follow in making a decision on the monthly physical condition of a woman who is using the apparatus 10. The woman depresses the power source switch 41a at STEP 1, thus putting the apparatus 10 in circuit with the power supply. Depression of the setting button 41f at STEP 2 puts the apparatus 10 in the setting mode, proceeding to Step 3 where the present date and time is set Specifically the digits representing date and time are changed by using the UP digit-shifting button 41c and the DOWN digit-shifting button 41d until the present date and time has appeared in the display, and then, the present date and time are set by depressing the setting button 41f again. Likewise, the beginning day of the previous menstruation period is inputted and set. The weight the woman desires is inputted and set at STEP 4. If not, the apparatus 10 performs an arithmetic operation to determine and set an ideal weight from the height and age of the woman, which are inputted by her.

Depression of the measurement button 41b at STEP 5 makes the measurement mode proceed to STEP 6. If not, the apparatus is put in the menstruation data inputting mode, proceeding to STEP 15.

The measurement mode starts from STEP 5. The woman stands on bare feet on the bioelectrical impedance meter 20 equipped with the weight scale. Specifically she stands on the weight scale with the toes and heels of the left and right feet put on the constant current feeding electrodes 21a and 21b and the voltage measuring electrodes 22a and 22b respectively. Then, the measurement starts with the weight of the woman.

At STEP 7 the high-frequency, constant current circuit 23 makes a high-frequency, weak current flow in her body via the constant current feeding electrode 21a, the toe of the left foot, the left leg, the lower part of her abdomen, the right leg, the toe of the right foot and the constant current feeding electrode 21b. The voltage measuring circuit 24 determines the voltage appearing between the voltage measuring electrodes 22*a* and 22*b*, thus determining the BI value. At STEP 8 the BI value is modified with weight according to the equation 1 or 2 as described above.

At STEP 9 the BI values measured several days before the present day, the physical condition determined on the day before the present day, the beginning day of the last menstruation period and other data are retrieved from the memory 44 to be put in the CPU 45.

At STEP 10, on the basis of the relation between the BI values and the monthly body condition as described earlier, and from the weight-modified BI values measured this time and some data retrieved from the memory 44 at STEP 9, the CPU 45 makes a decision as to which divisional period the woman is passing over, the First Divisional Period (the menstruation period), the Second Divisional Period (the "in good condition" period), the Third Divisional Period (the "not changing" period), the Fourth Divisional Period (the "in poor condition" period) and the Fifth Divisional Period (the pregnancy-possible period).

At STEP 11 the CPU 45 responds both to the physical condition determined at STEP 10 and to the difference between the set weight and the present weight measured at STEP 6 for selecting an advisory message most appropriate for the purpose of controlling and managing her body condition among those stored in the memory 44. Thus, the display 42 shows the so selected advisory message. As described earlier, women's basal metabolic rate rises after the ovulation day, and women's body temperature rises after the ovulation day, also. The amount of calorie women are consuming while exercising rises, too. Therefore, the advisory message say, "Do dieting."

The amount of dieting recommendable for the weight difference of 2 or less kilograms is given as Dieting Level 1; the amount of dieting recommendable for the weight difference of 2 to 5 kilograms is given as Dieting Level 2; and the amount of dieting recommendable for the weight difference of 5 or more kilograms is given as Dieting Level 3. Advisory messages are selected in terms of "Dieting Level". The CPU 45 identifies the advisory message in terms of their identification numbers to prevent same advisory message as shown lately from being repeated.

At STEP 12 the display 42 shows the advisory message selected at STEP 11. FIG. 7 shows some examples of advisory messages. When the present weight is equal to the set weight or even lighter than the set weight, no advisory message pertaining to the weight and dieting is presented, and a general advice is given as is the case with the first embodiment.

At STEP 13 the weight-modified BI value measured this time, the present body condition, the date of measurement, the identification numbers of the advisory messages actually presented and some other data are stored in the memory 44. Then, at STEP 14 the power supply turns off automatically, and the measurement ends.

At STEP 15 the menstruation data inputting mode starts. A desired date is given in the display 42 by depressing the UP digit-shifting button 41*c* and the DOWN digit-shifting button 41*d*. At STEP 16 a decision is made as to whether or not the menstruation beginning day inputting button 41*e* was depressed. In the affirmative, the date selected at STEP 15 is stored in the memory 44 as the beginning day of the coming menstruation period. In the negative, at STEP 16 a decision is made as to whether or not the power source button 41*a* was depressed. In the affirmative, the power supply turns off at STEP 14, and the inputting of data is finished.

Division of periods pertaining to the monthly body condition may be different from those described above, and adjacent divisional periods may overlap a few days. The swelling or dieting levels described above should be understood as mere examples. Advisory messages are described as being presented in the display, but advisory contents may be given in the form of pictures rather than words. Otherwise, a collection of advisory messages and lamps allotted thereto may be used, and a selected lamp is lit to indicate which advisory message is selected. A selected advisory message may be presented orally.

Described below is a female physical condition managing apparatus 60 according to the third embodiment, which permits a female user to make a decision readily on her monthly body condition from the graphic presentation of BI values measured each and every day.

Referring to FIG. 8, the female physical condition managing apparatus 60 comprises a scale-and-bioelectrical impedance meter 70 and a control box 90 connected to the scale-and-bioelectrical impedance 70 via an electric cable 80 or via infrared or electromagnetic wave.

The scale-and-bioelectrical impedance meter 70 has constant current feeding electrodes 71*a* and 71*b* and voltage measuring electrodes 72*a* and 72*b* provided on its front side whereas the control box 90 has a set of operation buttons 91*a* to 91*f* and a display 92 provided on its front side. The set of operation buttons include a power source button 91*a*, a measurement button 91*b*, an UP digit-shifting button 91*c*, a DOWN digit-shifting button 91*d*, a "menstruation beginning day" inputting button 91*e*, a setting button 91*f* and a graph button 91*g*.

Figure 9:
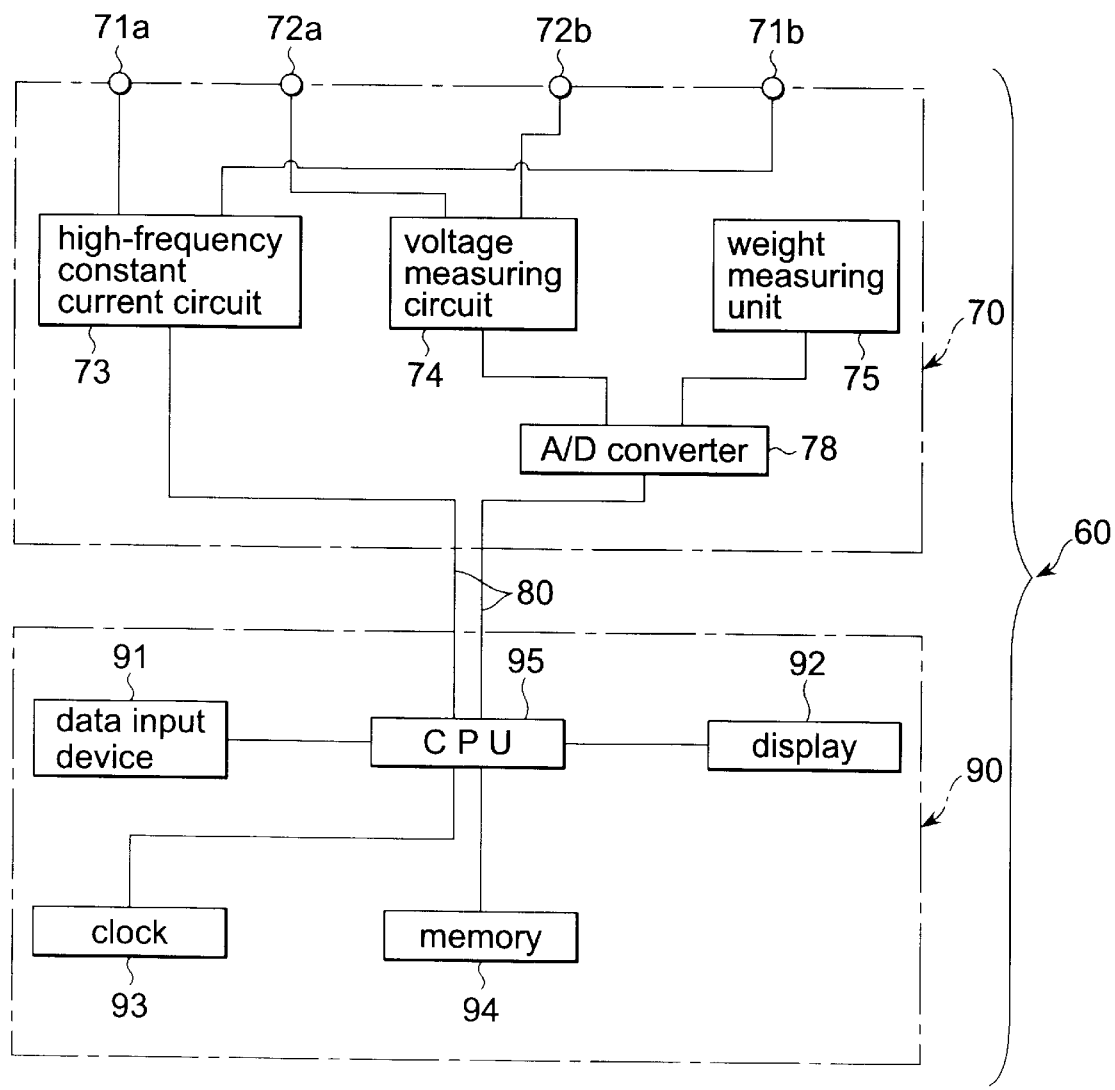
FIG. 9 shows how different functions make up the female physical condition managing apparatus of FIG. 8.

FIG. 9 shows the functional structure of the female physical condition managing apparatus 60. As shown, the scale-and-bioelectrical impedance meter 70 comprises a high-frequency constant current circuit 73 for supplying a weak high-frequency current of fixed value to the constant current feeding electrodes 71*a* and 71*b*, a voltage measuring circuit 74 for measuring the voltage appealing between the voltage measuring electrodes 72*a* and 72*b*, a weight measuring unit 75, and an A/D converter 78 for converting the measured voltage and weight to digital values.

The control box 90 comprises a data input device 91 including a set of operation buttons 91*a* to 91*g* for inputting instructions for measurement, data pertaining to the menstruation period and other pieces of information, a display 92 for showing the time-sequence transition of measured BI values, the body condition and such like, a clock 93 for determining the date and time on and at which the measurement is effected, a memory 94 for storing the measured BI values, the date and time of measurement, the body conditions determined and other pieces of information, and a CPU 95 which takes not only the part of making a decision about the woman's body condition on the basis of the data pertaining to the menstruation period, measured weight and BI value but also the part of attaining the arithmetic operation required for controlling the storage of a variety of data in the storage or presentation of some selected data in the display 92.

In this particular embodiment the scale-and-bioelectrical impedance meter 70 and the control box 90 are separate, together making up the female physical condition managing apparatus. The CPU 95 may be installed in the scale-and-bioelectrical impedance meter 70. Otherwise, the scale-and-bioelectrical impedance meter 70 and the control box 90 may be combined as a whole.

Now, the manner in which the female physical condition managing apparatus works is described.

Figure 10:
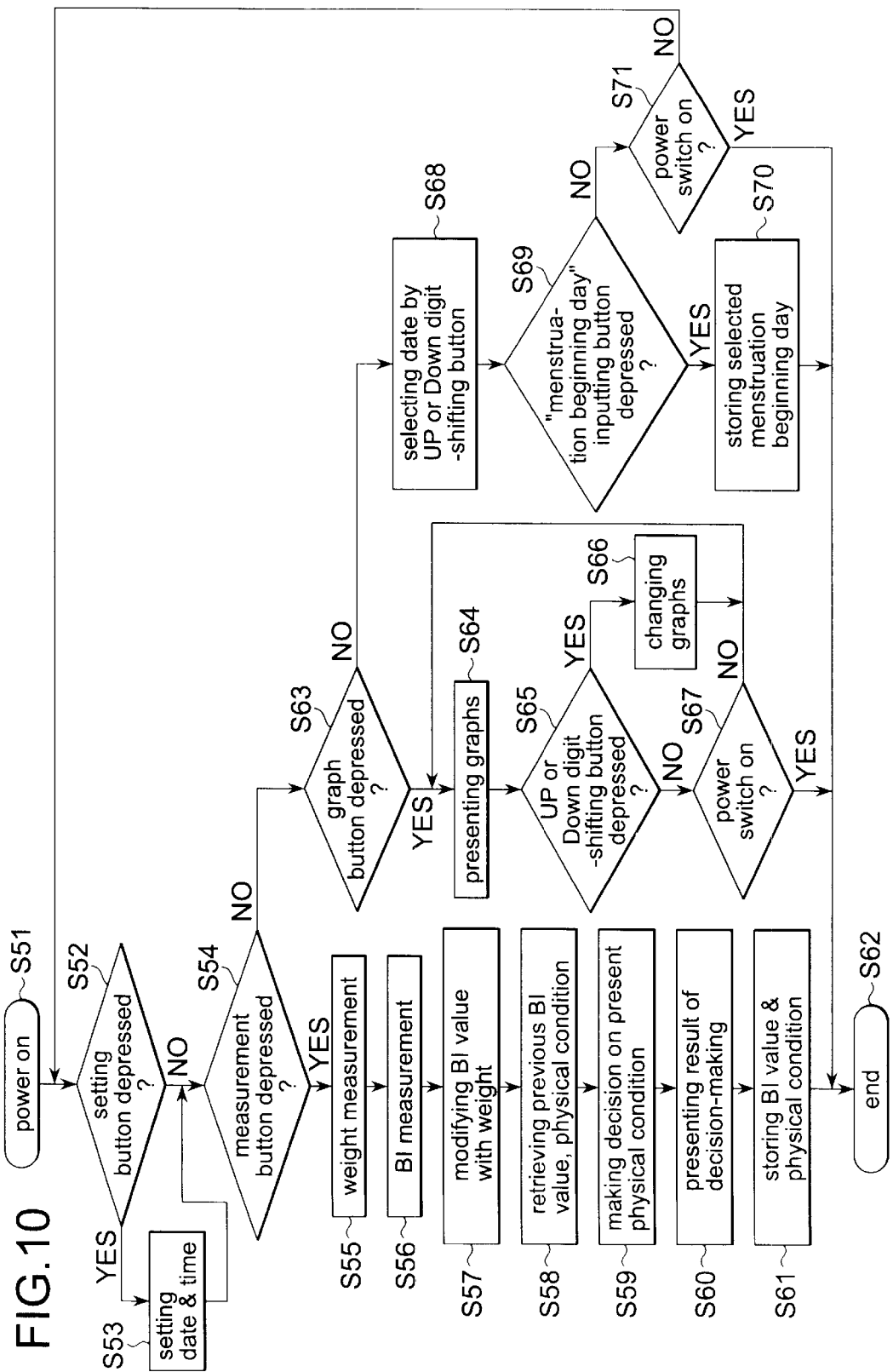
FIG. 10 is a flowchart showing the proceeding according to which the female physical condition managing apparatus of FIG. 8 works.

FIG. 10 is a flow chart showing the sequential steps to follow in making a decision on the monthly physical condition of a woman who is using the apparatus 60. The woman depresses the power source switch 91a at STEP 51, thus putting the apparatus 60 in circuit with the power supply. Depression of the setting button 91f at STEP 52 puts the apparatus 60 in the setting mode, proceeding to Step 53 where the present date and time is set. Specifically the digits representing date and time are changed by using the UP digit-shifting button 91c and the DOWN digit-shifting button 91d until the present date and time has appeared in the display, and then, the present date and time are set by depressing the setting button 91f again. Likewise, the beginning day of the menstruation period is inputted and set.

Depression of the measurement button 91b at STEP 54 puts the apparatus 60 in the measurement mode, proceeding to STEP 55. If not, the apparatus 60 is put in the menstruation data inputting mode, proceeding to STEP 64.

The measurement mode starts from STEP 55. The woman stands on her barefoot on the bioelectrical impedance meter 70 equipped with the weight scale. Specifically she stands on the weight scale with the toes and heels of the left and right feet put on the constant current feeding electrodes 71a and 71b and the voltage measuring electrodes 72a and 72b respectively. Now, the measurement starts with the weight of the woman.

At STEP 56 the high-frequency, constant current circuit 73 makes a high-frequency weak current flow in her body via the constant current feeding electrode 71a, the toe of the left foot, the left leg, the lower part of her abdomen, the right leg, the toe of the right foot and the constant current feeding electrode 71b. The voltage measuring circuit 74 determines the voltage appearing between the voltage measuring electrodes 72a and 72b, thus determining the BI value. At STEP 57 the BI value is modified with weight according to the following equation 1 or 2:

$$BI \text{ modified with weight} = BI + A \times (\text{difference of weight from the initial weight}), \quad (1)$$

or $$BI \text{ modified with weight} = BI + B \times (\text{difference of weight from the preceeding weight}), \quad (2)$$

where "A" and "B" stand for correction coefficients.

The so modified BI value is independent from the influence caused by the varying weight.

At STEP 58 the BI values measured on several days before the present day, the physical condition determined on the day before the present day, some data pertaining to the beginning day of the last menstruation period and other data are retrieved from the memory 94 to be put in the CPU 95.

At STEP 59 on the basis of the relation between the BI values and the monthly body condition as described earlier, and in consideration of the weight-modified BI value measured this time at STEP 57, those values measured previously and stored in the memory 94, the physical condition determined lastly, the beginning day of the menstruation period and other data, all of which are retrieved from the memory 94 and inputted in the CPU 95 at STEP 58 the CPU 95 makes a decision as to which divisional period the woman is passing over, the First Divisional Period (the menstruation period), the Second Divisional Period (the "in good condition" period), the Third Divisional Period (the "not changing" period), the Fourth Divisional Period (the "in poor condition" period) or the Fifth Divisional Period (the pregnancy-possible period). The description of the decision-making is omitted because it is described earlier in connection with the first embodiment.

Figure 11:
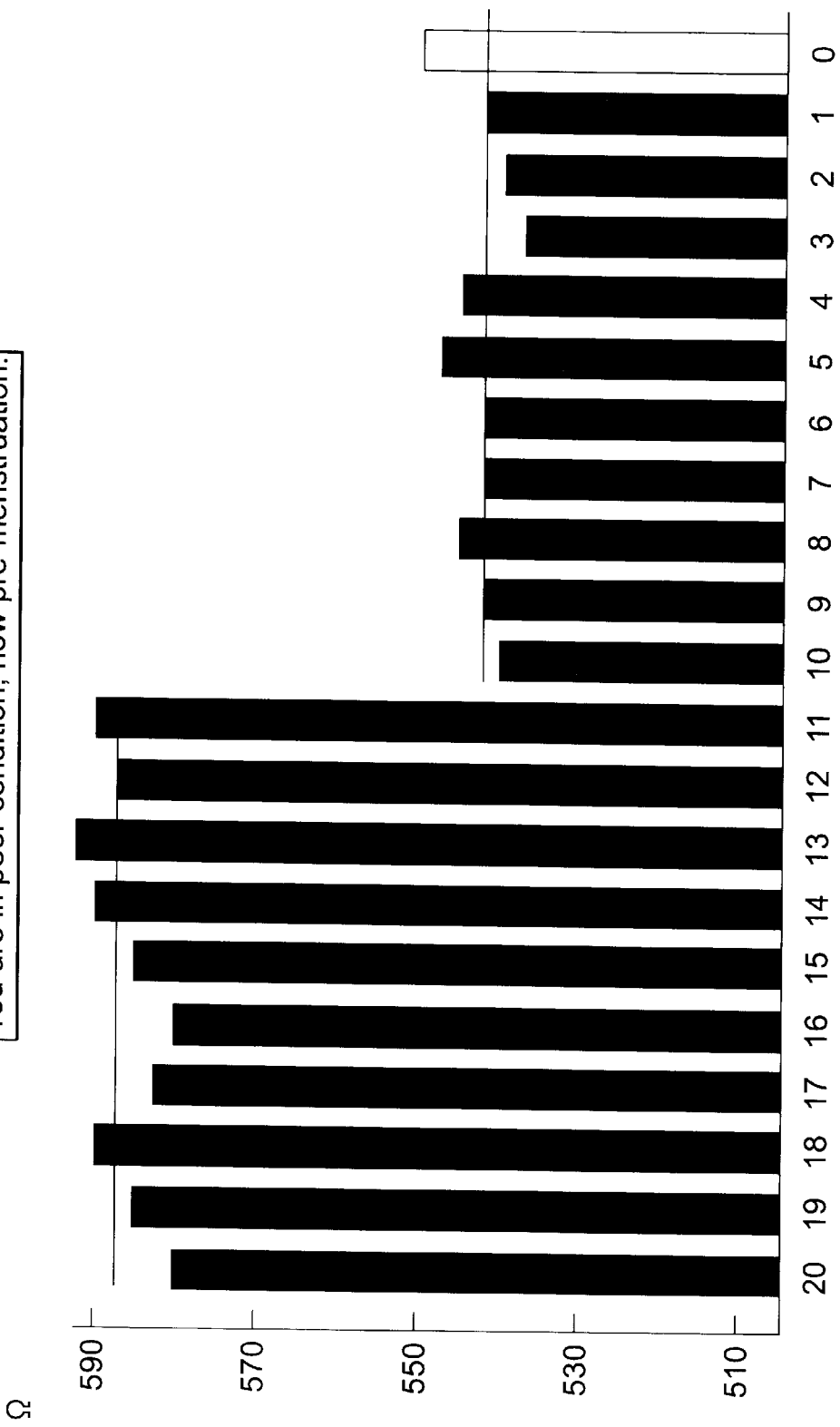
FIG. 11 shows one example of the graphic presentation.

In FIG. 11, At STEP 60 a graphic presentation is given in the display 42, showing how the BI value varies in the divisional periods, which are characteristic of different aspects appearing in the monthly body condition. The graph shows the BI values measured each of 20 days before the day on which the measurement was made. In the bar graph all of the preceding BI values are given in solid black, and the BI value measured this time is given in white blank. In addition, the mean values in the high-value and low-value sections of the twenty day-long period are given in solid line; the high-value section includes the first and second divisional periods, and the low-value section includes the third and fourth divisional periods. From the average line and the present BI value the woman can realize readily how her body condition is proceeding. At STEP 61 the weight-modified BI value measured this time, the weight, the date of measurement and other data are stored in the memory 94. Then, the power supply turns off at STEP 62, thus terminating the measurement.

Figure 12:
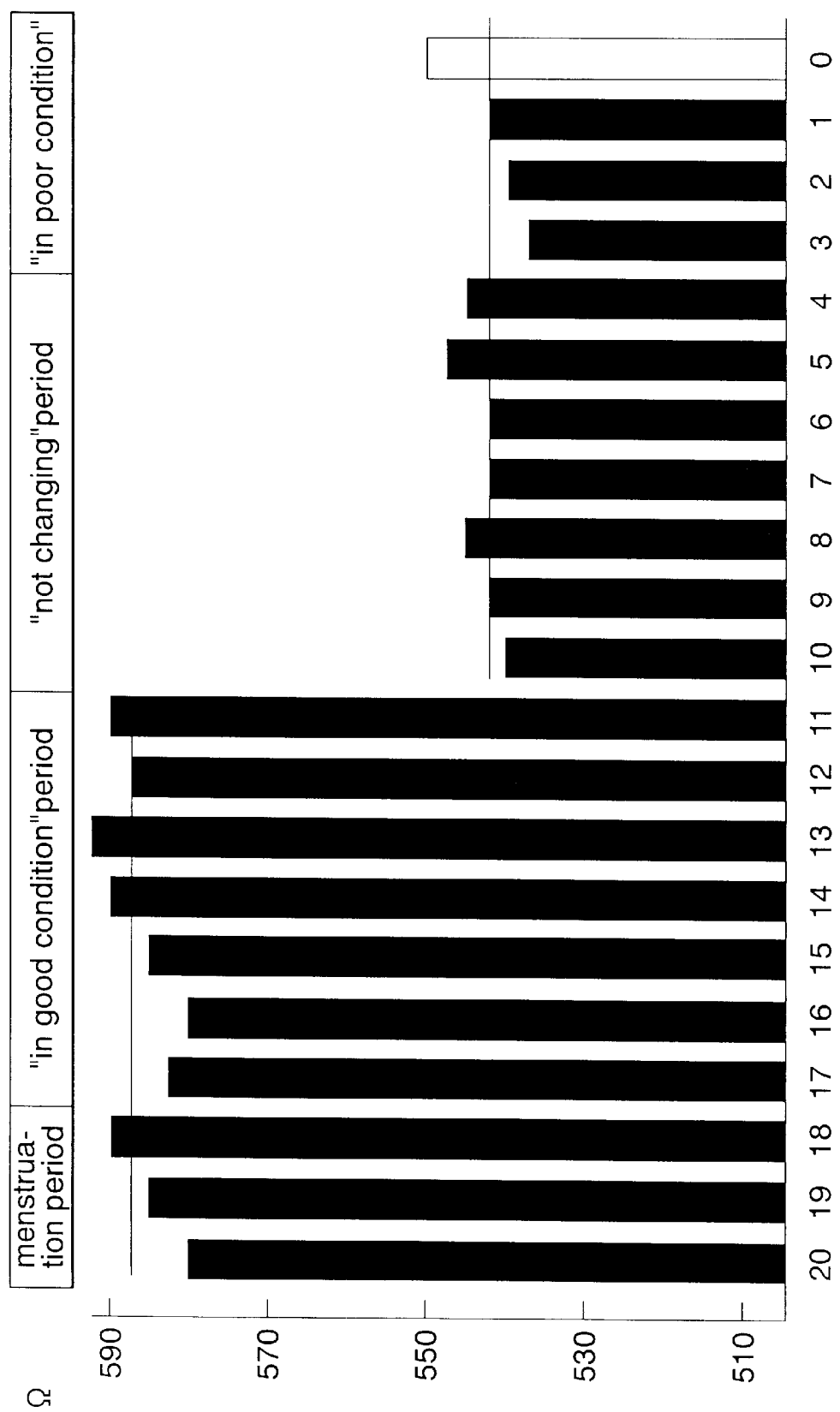
FIG. 12 shows another example of the graphic presentation.

At STEP 63 the graphic presentation mode starts. A decision is made as to whether the graph button 91g is depressed or not. In the affirmative the graph of FIG. 12 appears at STEP 64. It is same as the graph of FIG. 11 except for the indication of the aspects appearing in the divisions of the twenty day-long period, thereby facilitating the understanding of which stage has been reached and, at the same time, what body condition is supposed to appear.

At STEP 65 a decision is made as to whether the UP digit-shifting button 91c or the DOWN digit-shifting button 91d was depressed or not. In a case where the DOWN digit-shifting button 91d was depressed, the graph of FIG. 13 appears at STEP 66. Another depression of the DOWN digit-shifting button 91d changes it for the graph of FIG. 14 at STEP. Every time the DOWN digit-shifting button 91d is depressed, the graph is changed, allowing those of FIGS. 12, 13 and 14 to appear sequentially in the order named at STEP 66, and final depression of the DOWN digit-shifting button 91d allows the graphic presentation to return to the graph of FIG. 12. Every time the UP digit-shifting button 91c is depressed, the graph is changed conversely to allow those of FIGS. 12, 14 and 13 to appear sequentially in the order named at STEP 66 and final depression of the UP digit-shifting button 91c allows the graphic presentation to return to the graph of FIG. 12.

Figure 13:
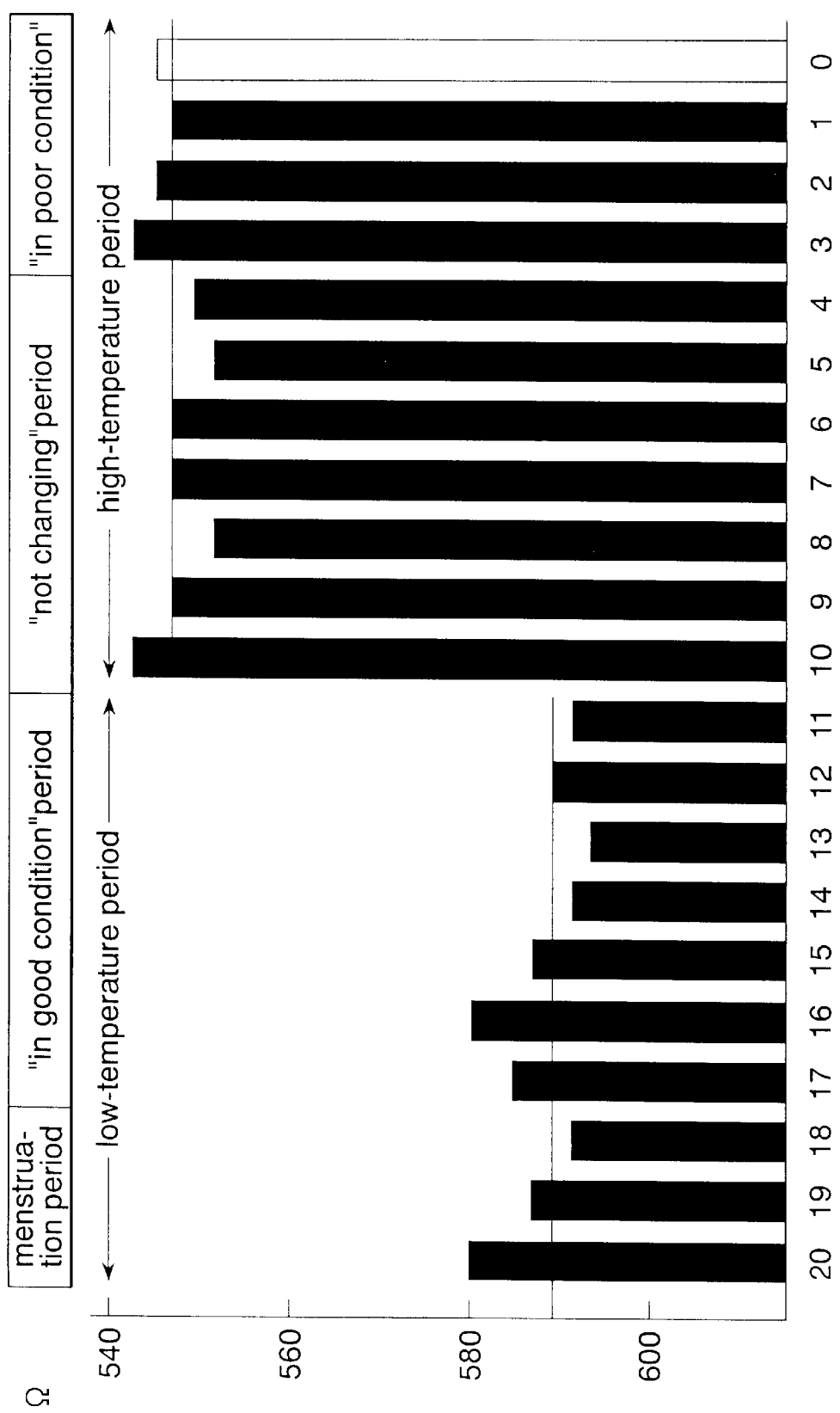
FIG. 13 shows still another example of the graphic presentation.

In the graph of FIG. 13 the ordinate value of BI decreases upward, and increases downward. The manner of graphic presentation is converse to FIGS. 11 and 12. In the graph of FIG. 13 the low-body temperature period and the high-body temperature period are indicated; the former covers the first and second divisional periods whereas the latter covers the third and fourth divisional periods.

The converse graphic presentation of BI values in FIG. 13 looks like the graphic presentation of body temperatures, the values of which remain low after termination of the menstruation period and high after the ovulation day. Women are familiar with the graphic presentation of body temperature plotted by measuring their body temperature every day, and therefore, the converse graphic presentation of BI values in FIG. 13 permits women to realize their bodily conditions in the same manner as from the graphic presentation of body temperature.

Figure 14:
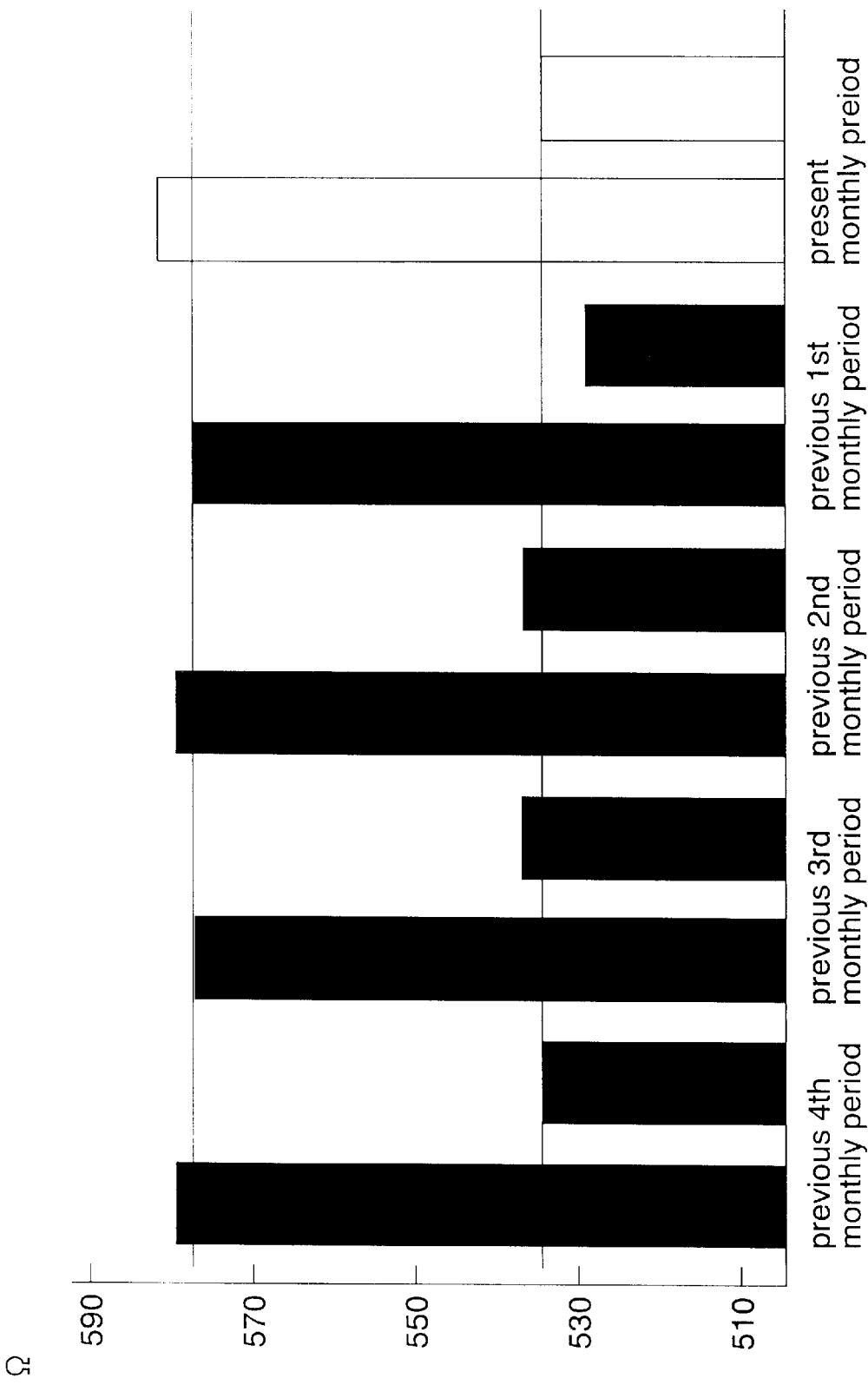
FIG. 14 shows yet still another example of the graphic presentation.

Referring to FIG. 14, the average values of BI are determined for the high-value and low-value sections each of the previous and last months, and these average values are shown in the form of bar graph. This facilitates monthly comparison of BI values, thus permitting women to understand the long-termed variation at first glance.

In a case where neither UP digit-shifting button 91c nor DOWN digit-shifting button 91d are found to have been depressed at STEP 65, a decision is made as to whether the electric power switch 91d was depressed or not at STEP 67. In the affirmative, the electric power supply turns off at STEP 62. In the negative the proceeding returns to STEP 64 where the graph now selected continues to appear in the display.

The menstruation period data inputting mode starts at STEP 68. The date the woman desires is selected and shown in the display 92 by depressing the UP digit-shifting or DOWN digit-shifting buttons 91c and 91d. A decision is made as to whether the menstruation beginning day inputting button 91e was depressed. In the affirmative, the selected date is stored as the beginning day of the menstruation period in the memory 94. In the negative, a decision is made as to whether the electric power source switch 91a was depressed. In the affirmative, the electric power source turns off at STEP 62. Then, the inputting operation is completed.

Two-dimensional bar graphs are shown by way of example. Three-dimensional graphs or line graphs may be equally used.

Weight-modified BI values are used, but BI values can be used without being modified with weight for the practical purpose. BI values may be measured by measuring voltage appearing between both hands or between one hand and one foot rather than both feet.

As may be understood from the above, the female physical condition managing apparatus according to the third embodiment permits a female user to facilitate the decision-making on her monthly body condition in terms of BI values, which are shown graphically in two separate sections, that is, the high-body temperature period and the low-body temperature period. An average line of BI values appears in each section, thereby making it still easy to make a decision on her body condition.

The converse graphic presentation of BI values makes women feel familiar with the graphic presentation of BI values because of similar appearance to the graphic presentation of body temperatures, which women get used to for health care.

The graphic presentation can be given quickly, and therefore, the apparatus can be conveniently used when getting up in the morning, and there is no fear of oversleeping as is the case with measuring their body temperature with thermometers in bed.

What is claimed is:

1. A female physical condition managing apparatus comprising:
   a plurality of pairs of electrodes;
   a bioelectrical impedance meter;
   an advice storing device;
   a decision-making unit;
   an advising unit; and
   an informing unit, wherein
      said pairs of electrodes can be applied to selected points of the outer layer of the skin of a woman's body;
      said bioelectrical impedance meter measures the value of BI appearing between one of said pairs of electrodes;
      said advice storing device stores a plurality of advisory messages for each of the specific divisional periods characteristic of the different phases which are noticeable from the monthly body condition of the woman;
      said decision-making unit makes a decision as to which specific divisional period the woman is passing over on the basis of a time-series transition of BI;
      said advising unit is responsive to the decision-making of which specific divisional period for retrieving appropriate advisory messages from the advice storing device; and
      said informing unit informs the woman of the so retrieved advisory message;
      wherein the advice storing device may have advisory messages stored for each of the first divisional period spanning from the beginning day to the ending day of the menstruation period, the second divisional period spanning from the day subsequent to the termination of the menstruation period to the ovulation day, the third divisional period spanning from the ovulation day to the specific day one week earlier than the beginning of next menstruation period presumable from the record, and the fourth divisional period spanning from the specific day to the beginning day of next menstruation period.

2. A female physical condition managing apparatus according to claim 1 wherein the advice storing device has advisory messages stored for the fifth pregnancy-possible period.

3. A female physical condition managing apparatus according to claim 1 or 2 wherein the decision-making unit includes a swelling determining unit, which is responsive to the decision-making of the present period being the fourth divisional period for determining the degree of swelling in terms of the value of BI determined by the bioelectrical impedance meter, and for retrieving the most appropriate advisory message from the advise storing device.

4. A female physical condition managing apparatus according to claim 1 wherein it further comprises:
   an inputting unit;
   a weight scale; and
   a weight difference arithmetic unit, wherein:
      said inputting unit sets and inputs a desired weight;
      said weight scale measures the present weight; and
      said weight-difference arithmetic unit determines the difference between the desired weight and the present-weight, whereby
      the advising unit may retrieve appropriate advisory messages from the advise storing device on the basis of the difference between the desired weight and the present weight and the divisional period representing the current body condition.

5. A female physical condition managing apparatus according to claim 4 wherein the value of BI is the one modified with the weight measured by the weight scale.

6. A female physical condition managing apparatus according to claim 4 or 5 wherein the appropriate advisory message pertain to the weight and the dieting.

7. A female physical condition managing apparatus according to claim 4 wherein in a case where the divisional period determined by the decision-making unit is the third divisional period, the appropriate advisory messages pertaining to the weight and the dieting induce the woman to perform dieting positively.

8. A female physical condition managing apparatus comprising:
   a bioelectrical impedance meter;
   a bioelectrical impedance memory;
   an arithmetic unit; and
   a display, wherein
      said bioelectrical impedance meter measures the value of BI of a woman who is using the apparatus;
      said bioelectrical impedance memory stores the measured values of BI;

said arithmetic unit calculates the mean value of the values of BI stored for the period for which the BI remains at raised values and the mean value of those stored for the period for which the BI remains at lowered values; and said display displays the time-sequence transition of the stored BI values in the form of graphs, and said display displays the mean values of the raised and lowered values of BI calculated by said arithmetic unit in the form of graphs.

9. A female physical condition managing apparatus comprising:

a bioelectrical impedance meter;

a bioelectrical impedance memory; and a display, wherein said bioelectrical impedance meter measures the value of BI of a woman who is using the apparatus said bioelectrical impedance memory stores the measured values of BI; and said display displays the time-sequence transition of the recorded values of BI in the form of graphs, representing time in abscissas and the values of BI in ordinates, the value of BI increasing with the descending distance toward the axis of abscissas, whereby the envelope of the raised values of BI may be low whereas the envelope of the lowered values of BI may be high.

10. A female physical condition managing apparatus according to claim 8 or 9 wherein it further comprises a decision-making unit wherein said decision-making unit makes a decision on which specific divisional period of the monthly physical condition the woman is passing over on the basis of the time-sequence transition of BI, allowing the display to show the present physical condition along with the graphic presentation.

11. A female physical condition managing apparatus according to claim 8 or 9 wherein it further comprises:

a decision-making unit; and a physical condition memory, wherein:

said decision-making unit makes a decision on which specific divisional period of the monthly physical condition the woman is passing over on the basis of the time-sequence transition of BI; and said physical condition memory stores the physical conditions determined by the decision-making unit, thus allowing the display to show in the graphic presentation, the divisional period for which the woman has passed over for reference.

12. A female physical condition managing apparatus according to claim 8 or 9 wherein it further comprises a body temperature presuming unit, wherein said body temperature presuming unit makes a decision as to whether the body temperature varies in the high-temperature period or the low-temperature period from the time-sequence transition of the BI values stored in the bioelectrical impedance memory, thereby allowing the display to indicate in the graphic presentation, the high-temperature period of the low-temperature period thus presumed by the body temperature presuming unit.

13. A female physical condition managing apparatus comprising:

a bioelectrical impedance meter;

a bioelectrical impedance memory;

an arithmetic unit; and a display, wherein:

said bioelectrical impedance meter measures the value of BI of a woman who is using the apparatus;

said bioelectrical impedance memory stores the measured values of BI;

said arithmetic unit calculates the mean values per monthly period of the BI values of the high-temperature period and of those of the low-temperature period with reference to the monthly physical condition of the woman; and said display shows the mean values of the BI values of the high-temperature period and those of the low-temperature period in each of plural monthly periods in the form of a graph.

* * * * *

UNITED STATES PATENT AND TRADEMARK OFFICE
CERTIFICATE OF CORRECTION

PATENT NO. : 6,665,561 B2
DATED : December 16, 2003
INVENTOR(S) : Michiko Baba et al.

It is certified that error appears in the above-identified patent and that said Letters Patent is hereby corrected as shown below:

Title page,
Item [30], Foreign Application Priority Data, please change
"Feb. 10, 2000 (JP)..........2000-302756
 Feb. 10, 2000 (JP)..........2000-312434"
to
-- Oct. 2, 2000 (JP)..........2000-302756
   Oct. 12, 2000 (JP)..........2000-312434 --

Signed and Sealed this

Thirteenth Day of April, 2004

JON W. DUDAS
*Acting Director of the United States Patent and Trademark Office*